United States Patent [19]

Ashby et al.

[11] 4,436,924

[45] * Mar. 13, 1984

[54] ULTRAVIOLET LIGHT ABSORBING AGENTS AND COMPOSITIONS AND ARTICLES CONTAINING SAME

[75] Inventors: Bruce A. Ashby; Siegfried H. Schroeter, both of Schenectady, N.Y.

[73] Assignee: General Electric Company, Waterford, N.Y.

[*] Notice: The portion of the term of this patent subsequent to Jul. 14, 1998 has been disclaimed.

[21] Appl. No.: 421,797

[22] Filed: Sep. 23, 1982

Related U.S. Application Data

[62] Division of Ser. No. 225,429, Jan. 15, 1981, Pat. No. 4,374,674.

[51] Int. Cl.³ .................... C09K 3/00; C07F 7/18; C07F 7/09
[52] U.S. Cl. .................... 556/416; 106/287.12; 556/436
[58] Field of Search .................... 556/416, 436

[56] References Cited

U.S. PATENT DOCUMENTS

| Re. 27,281 | 2/1972 | Wilkus et al. | 260/46.5 |
|---|---|---|---|
| 3,352,896 | 11/1967 | Dressler | 260/448.8 |
| 3,395,116 | 7/1968 | Dressler | 260/45.95 |
| 3,489,781 | 1/1970 | Wilkus et al. | 260/46.5 |
| 3,708,225 | 1/1973 | Misch et al. | 351/160 |
| 3,976,497 | 8/1976 | Clark | 106/287 |
| 3,986,997 | 10/1976 | Clark | 260/29.2 |
| 4,042,613 | 7/1977 | Takamizawa et al. | 260/448.2 |
| 4,051,161 | 9/1977 | Proskow | 260/448.2 |
| 4,177,315 | 12/1979 | Ubersax | 428/336 |
| 4,278,804 | 7/1981 | Ashby et al. | 556/416 |
| 4,374,674 | 2/1983 | Ashby et al. | 106/287.12 |

OTHER PUBLICATIONS

Kaesz et al., J. Amer. Chem. Soc., 1957, pp. 1433–1435.

*Primary Examiner*—Theodore Morris
*Attorney, Agent, or Firm*—Hedman, Gibson, Costigan & Hoare

[57] ABSTRACT

There are provided ultraviolet light absorbing agents of the following general formula

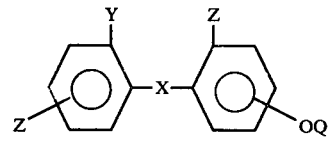

wherein:

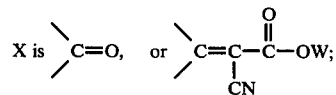

Y is H or OH,
Z is H, OH, OQ or OW, where at least one Z is OH if Y is H;
Q is $-CH_2(CH_2)_nSi(R_2)_x(OR_1)_y$; and
W is $-C_mH_{2m+1}$;

where $x=0$, 1 or 2, $y=1$, 2 or 3, $x+y=3$, $R_1$=alkyl or alkanoyl having 1 to 6 carbon atoms, $R_2$=alkyl having 1 to 6 carbon atoms, $n=0$, 1 or 2, and $m=1$ to 18. Also provided are organopolysiloxane protective coating compositions containing said ultraviolet light absorbing agents having unique utility for protecting transparent plastic articles.

This invention relates to new, improved ultraviolet light absorbing agents, as well as to articles primed and thereafter coated with compositions containing such agents. The novel compounds of this invention are silanolreactive alkoxysilyl- or alkanoyloxysilylalkyl ether adducts of aromatic ultraviolet absorbing agents.

3 Claims, No Drawings

ULTRAVIOLET LIGHT ABSORBING AGENTS AND COMPOSITIONS AND ARTICLES CONTAINING SAME

This is a divisional of application Ser. No. 225,429, filed Jan. 15, 1981 now U.S. Pat. No. 4,374,674.

BACKGROUND OF THE INVENTION

The use of transparent plastic materials in place of glass panels is becoming more widespread. For instance, transparent glazing made of synthetic organic polymers is now employed more frequently in transportation, such as trains, buses and the like, in optical equipment, and in contruction materials. In comparison with glass, transparent plastics are shatter-resistant and lighter in weight.

While enjoying the foregoing advantages, transparent plastics are nevertheless susceptible to scratching and marring on the surface, which impairs visibility and detracts from the physical appearance. Moreover, transparent plastics tend to undergo discoloration upon prolonged exposure to ultraviolet light, e.g., sunlight.

Attempts have been made to improve the abrasion resistance of transparent plastics. It has been proposed, for instance, that mar- or scratch-resistant coatings for such plastics can be prepared from mixtures comprising silica and hydrolyzable silanes in a suitable medium such as alcohol and water. Such protective coatings are described in Misch et al., U.S. Pat. No. 3,708,225, Clark, U.S. Pat. No. 3,986,997 and U.S. Pat. No. 3,976,497, and Ubersax, U.S. Pat. No. 4,177,315. Other scratch resistant protective coatings are described in copending applications Ser. No. 964,910 and Ser. No. 964,911, both filed Nov. 30, 1978, assigned to the same assignee as herein. Typically, these are applied to the primed surface of the transparent plastic and heat cured in situ.

Attempts have also been made to reduce the tendency of the coatings on transparent plastics toward deterioration on exposure to sunlight and the like by incorporating in the coating compositions materials which absorb ultraviolet light rays. A disadvantage of many such ultraviolet light absorbing materials is that they often escape from the compositions, e.g., by volatilization, usually during the heat curing cycle. Efforts to overcome this defect by using ultraviolet light absorbing materials having higher molecular weights, e.g., American Cyanamid's Cyasorb UV-531, have not been entirely successful.

Proskow, U.S. Pat. No. 4,051,161, discloses an alternative approach and this is to use a silicone-fluorohydroxy copolymer coating with a silanol-reactive functional derivative of an aromatic ultraviolet light-absorbing compound. As the agent to contribute the silanol-reactive functional group it is proposed to use a complex epoxysilane compound. The Proskow coating is not the preferred, less complex silica-hydrolyzable silane coating of the earlier-mentioned citations. Moreover, as is described in the commonly assigned, concurrently filed application of T-Y. Ching, Ser. No. 154,623, filed May 30, 1980, the new compounds are surprisingly adaptable for use in scratch resistant coatings for unprimed plastic surfaces, as well. Other commonly assigned, concurrently filed applications also deal with functionalized uv screens. See Ashby, Ser. No. 154,621 filed May 30, 1980 and T-Y. Ching, Ser. No. 154,625 filed May 30, 1980. The disclosures of the foregoing patents and applications are incorporated herein by reference.

It has now been discovered that reactive functional derivatives of aromatic ultraviolet light-absorbing agents with superior properties in all important respects can be obtained by using alkoxysilylalkyl- or alkanoyloxysilylalkylether functional groups, and that these are useful in the less complex systems, i.e., not the copolymer coating systems called for in U.S. Pat. No. 4,051,161.

With the new compounds of this invention scratch-resistant coatings for primed transparent plastics can be made more resistant to discoloration upon exposure to ultraviolet light. Because such modified ultraviolet light absorbers are adapted to co-react with the polysiloxane of the scratch-resistant coating composition there is a much reduced tendency of such materials to escape or oxidize during thermal processing. This provides substantial economy of use in comparison with the prior art.

DESCRIPTION OF THE INVENTION

According to this invention, there are provided new ultraviolet light absorbing agents having the following formula:

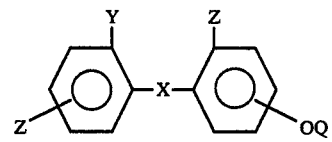

wherein:

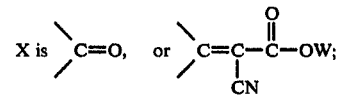

Y is H or OH;
Z is H, OH, OQ or OW, where at least one Z is OH if Y is H;
Q is —$CH_2(CH_2)_nSi(R_2)_x(OR_1)_y$; and
W is —$C_mH_{2m+1}$;
where x is 0, 1 or 2, y = 1, 2 or 3, x+y = 3, $R_1$ = alkyl or alkanoyl having 1 to 6 carbon atoms, $R_2$ = alkyl having 1 to 6 carbon atoms, preferably methyl, n = 0, 1 or 2 and m = 1 to 18.

Within the foregoing class, the following compounds are preferred:

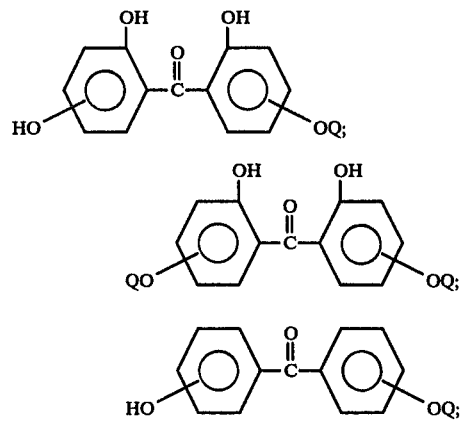

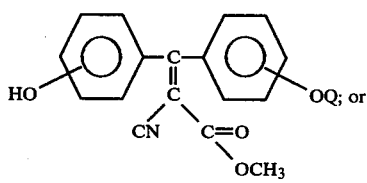

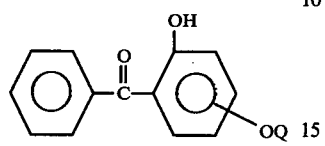

where Q is —CH$_2$Si(OCH$_3$)$_3$, —CH$_2$SiCH$_3$(OCH$_3$)$_2$, —CH$_2$Si(CH$_3$)$_2$(OCH$_3$), —CH$_2$(CH$_2$)$_2$Si(OCH$_3$)$_3$, —CH$_2$(CH$_2$)$_2$SiCH$_3$(OCH$_3$)$_2$, —CH$_2$(CH$_2$)$_2$Si(OCOCH$_3$)$_3$, —CH$_2$(CH$_2$)$_2$SiCH$_3$(OCOCH$_3$)$_2$, —CH$_2$(CH$_2$)$_2$Si(CH$_3$)$_2$—(OCOCH$_3$), —CH$_2$CH$_2$Si(OCH$_3$)$_3$, —CH$_2$CH$_2$SiCH$_3$(OCH$_3$)$_2$, or —CH$_2$CH$_2$Si(CH$_3$)$_2$(OCH$_3$). Special mention is made of the compound 4-[γ-(triethoxysilyl)propoxy]-2-hydroxybenzophenone.

This invention also includes articles comprising substrates, primed and thereafter coated with novel compositions comprising an effective amount of the described ultraviolet light absorbing agents and a dispersion of colloidal silica in an alipahtic alcohol-water solution of the partial condensate of a silanol having the formula RSi(OH)$_3$, where R is selected from the group consisting of alkyl having from 1 to 3 carbon atoms and aryl, at least 70 percent by weight of the silanol being CH$_3$Si(OH)$_3$. The dispersion contains from 10 to 50 percent by weight of solids, said solids consisting essentially of 10 to 70 percent by weight of colloidal silica and from 30 to 90 percent by weight of the partial condensate. Preferably, the dispersion has a pH of from 7.1 to about 7.8.

The ultraviolet light absorbing agents of this invention are prepared, for example, by a convenient method starting with a compound having the formula

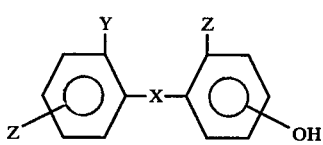

in which X, Y and Z are as defined above. In this method, one mole of the above compound is reacted in a solvent with one mole of a base, e.g., sodium methylate, to form a salt, e.g., a monosodium salt, which in turn is reacted with a halogenated alkoxysilane or alkanoyloxysilane having the formula ClCH$_2$(CH$_2$)$_n$Si(R$_2$)$_x$(OR$_1$)$_y$. Of course, other methods will be obvious to those skilled in this art.

For purposes of illustration, a suitable method may be represented as follows:

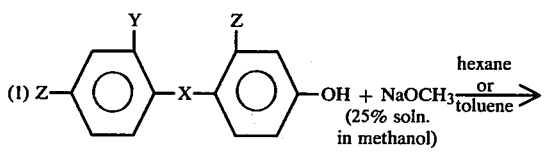

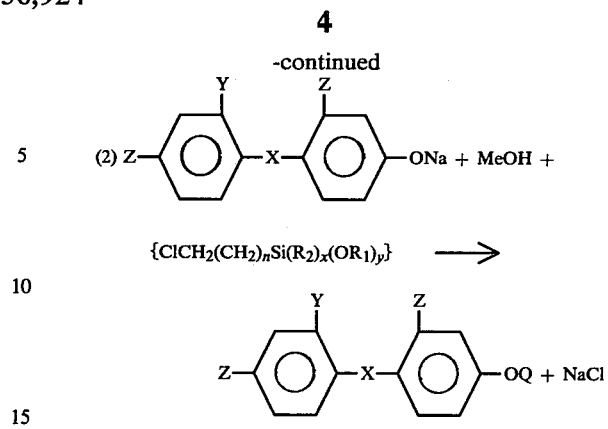

wherein X, Y, Z, Q, R$_1$, R$_2$, n, x and y are defined above.

In general, the reaction of sodium methylate and the starting compound containing the phenolic hydroxyl group can be run in the range between 20° and 65° C. for a period of 30 minutes to 2 hours. The reaction of the resulting sodium salt with the chloroalkoxysilane can be run in the range between 40° and 100° C. for a period of 2 to 6 hours. Yields of 50 to 80 percent are typical. The procedure can be run stepwise, in one vessel, followed by filtering off the by-product salt, stripping off the solvent and collecting the residue as the product. In the case of solid products, the residue can be recrystallized from an appropriate solvent, if desired.

The halogenated alkoxysilane for use in the above reaction are prepared, in good yield, by the platinum catalyzed reaction of alkenyl chloride with the corresponding alkoxysilyl hydride or acetoxysilyl hydride. Alternatively, these are prepared by reacting alkenyl chloride with the corresponding chlorosilane followed by alkoxylation or acyloxylation in known ways. Also, halogenated alkoxysilanes useful in this invention are prepared by alkoxylation of, for instance, the corresponding chloromethylchlorosilane. Procedures for preparation of the foregoing are described in the literature, e.g., G. H. Wagner, U.S. Pat. No. 2,637,838 and by H. D. Kaesze and F. G. A. Stone, J. Chem. Soc. (1957) 1433; see also, C. Eaborn, Organosilicon Compounds, Butterworths Scientific Publications, London, 1960.

An alternative method for making the new compounds herein comprises forming an allyl ether of a diarylketone, e.g., 2,4-dihydroxybenzophenone by reaction thereof with allyl bromide in refluxing acetone in the presence of potassium carbonate, then silylating the 4-allyloxy-2-hydroxybenzophenone with an alkoxy or acyloxysilane in the presence of a platinum catalyst in toluene. Further details are set forth in the commonly-assigned patent application of T-Y Ching, Ser. No. 154,623, filed concurrently herewith.

The coating compositions of this invention are prepared by hydrolyzing an alkyltrialkoxysilane or aryltrialkoxysilane having the formula RSi(OR)$_3$, where R is alkyl having 1 to 3 carbon atoms, or aryl, preferably phenyl, in an aqueous dispersion of colloidal silica to obtain a reaction product, and adding the described ultraviolet light absorbers to the resulting reaction product.

In general, the aqueous dispersion of colloidal silica is characterized by a particle size of from 5 to 150 millimicrons, and preferably from 10 to 30 millimicrons average diameter. Such dispersions are known in the art.

Commercially available materials include Ludox (DuPont) and Nalcoag (NALCO Chemical Co.). These are available in the form of acidic or basic hydrosols. With regard to this invention, if the pH of the coating composition is basic, then usually a basic colloidal silica sol is preferred for use in the composition. On the other hand, colloidal silicas which are initially acidic but which have been adjusted to be basic can also be used. It has been found that colloidal silica having a low alkali content, e.g., less than 0.35% by weight as $Na_2O$, provides a more stable coating composition, and these are preferred.

In preparing the compositions, the aqueous dispersion of colloidal silica is added to a solution of a small amount, e.g., from 0.07 to 0.10 percent by weight, of an alkyltriacetoxysilane, alkyltrialkoxysilane or alkyltrialkoxysilane or aryltrialkoxysilane. The temperature of the reaction mixture is kept in the range between 20° to 40° C., preferably below 25° C. A reaction time of about six to eight hours in usually sufficient to react enough of the trialkoxysilane such that the initial two-phase liquid mixture has been converted to a single liquid phase in which the silica is dispersed. Hydrolysis is permitted to continue for a period of 24 to 48 hours, depending on the desired final viscosity. As a rule, the longer the time permitted for hydrolysis, the higher the final viscosity.

During the preparation of the coating compositions, the alkyltriacetoxysilane is employed to buffer the viscosity of the initial two-phase liquid reaction mixture, and also to regulate the hydrolysis rate. Preferred are those alkyltriacetoxysilanes in which the alkyl group contains from 1 to 6 carbon atoms, and especially 1 to 3 carbon atoms. Methyltriacetoxysilane is the most preferred. Although alkyltriacetoxysilanes are preferred for use, it is to be understood that glacial acetic acid or other acids may be used instead. Such other acids include organic acids, such as propionic, butyric, citric, benzoic, formic, oxalic, and the like.

After hydrolysis has been complerted, the solids content of the coating composition is adjusted by adding alcohol to the reaction mixture. Suitable alcohols include lower aliphatics, e.g., having 1 to 6 carbon atoms, such as methanol, ethanol, propanol, isopropanol, n-butyl alcohol, t-butyl alcohol, and the like, or mixtures thereof. Isopropanol is preferred. The solvent system, i.e., mixture of water and alcohol, should contain from about 20 to 75 percent by weight of the alcohol to ensure that the partial siloxanol condensate is soluble.

Optionally, additional water-miscible polar solvents, e.g., acetone, butyl cellosolve, or the like, can be included in minor amounts, usually no more than 20 percent by weight of the solvent system.

After adjustment with solvent, the coating composition preferably has a solids content of from about 18 to about 25 percent by weight, especially preferably about 20 percent by weight of the total composition.

The coating composition has a pH of from about 3.5 to about 8, preferably, from about 7.1 to about 7.8, and especially preferably about 7.2 to about 7.8. If necessary, a base, such as dilute ammonium hydroxide, or weak acid, such as acetic acid, is added to adjust the pH within this range.

The silanetriols, $RSi(OH)_3$, are formed in situ as a result of admixing the corresponding trialkoxysilanes with the aqueous medium, i.e., the aqueous dispersion of colloidal silica. Examples of the trialkoxysilanes are those containing methoxy, ethoxy, isopropoxy and n-butoxy substituents which, upon hydrolysis, generate the silanetriols and further liberate the corresponding alcohol, e.g., methanol, ethanol, isopropanol, n-butanol, and the like. In this way, at least a portion of the alcohol content present in the final coating composition is provided. Upon generation of the hydroxyl substituents to form

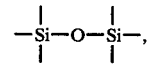

bonding occurs. This condensation, which takes place over a period of time, is not exhaustive but rather the siloxane retains a quantity of silicon-bonded hydroxyl groups which render the polymer soluble in the alcohol-water solvent mixture. This soluble partial condensate can be characterized as a siloxanol polymer having at least one silicon-bonded hydroxyl group for every three

units.

The portion of the coating composition which consists of non-volatile solids is a mixture of colloidal silica and the partial condensate (or siloxanol) of a silanol. The major portion or all of the partial condensate or siloxanol is obtained from the condensation of $CH_3Si(OH)_3$. Depending on the input of ingredients to the hydrolysis reaction, minor amounts of p tial condensate can be obtained, e.g., such as from the condensation of $CH_3Si(OH)_3$ with $C_2H_5Si(OH)_3$ or $C_3H_7Si(OH)_3$, of $CH_3Si(OH)_3$ with $C_6H_5Si(OH)_3$, or mixtures of the foregoing. For best results, it is preferred to use only methyltrimethoxysilane (thus generating all monomethylsilanetriol) in preparing the coating compositions. In the preferred embodiments, the partical condensate is present in an amount of from about 55 to 75 percent by weight, (the colloidal silica being present in an amount of from about 25 to about 45 percent by weight) based on the total weight of solids in the solvent comprising a mixture of alcohol and water. The alcohol comprises from about 50% to 95% by weight of the solvent mixture.

The coating compositions completely cure to hard coatings at a temperature of about 120° C., without the necessity of a curing catalyst. If milder curing conditions are desired, it is preferred to include a buffered latent condensation catalyst. Such catalysts are known to those skilled in the art. Examples include alkali metal salts of carboxylic acids, such as sodium acetate, potassium formate, and the like, amine carboxylates, such as dimethylamine acetate, ethanolamine acetate, dimethylaniline formate, and the like; quaternary ammonium carboxylates, such as tetramethylammonium acetate, benzyltrimethylammonium acetate, and the like; metal carboxylates, such as tin octoate; amines, such as triethylamine, triethanolamine, pyridine, and the like; and alkali hydroxides, such as sodium hydroxide, ammonium hydroxide, and the like. It should be noted that commercially available colloidal silicas, particularly those having a basic pH, i.e., above 7, contain free alkali metal base, and alkali metal carboxylate catalysts are generated in situ during hydrolysis.

The amount of the curing catalyst can vary widely, depending upon particular requirements. In general, the catalyst is present in an amount of from about 0.05 to about 0.5 and preferably about 0.1 percent by weight of the total coating composition. Such compositions are curable on the substrate within a brief period of time, e.g., from 30 to 60 minutes, using temperatures in the range from about 85° to about 120° C. A transparent, abrasion-resistant coating results.

The ultraviolet light-absorbing reaction products of this invention are added to the described coating composition before, during or after hydrolysis, and also before or after addition of solvent to adjust the solids. In preferred compositions, the ultraviolet light absorbing agents of this invention are used in amounts of from about 1.0 to about 25.0, preferably from 5.0 to 10.0 parts by weight per 100 parts by weight of said composition on a solids basis.

Other ingredients may also be added. Special mention is made of polysiloxane-polyether copolymers, which control flow and prevent flow marks, dirt marks, and the like, on the coating surface. Such materials also increase the stress cracking resistance of the coating.

Preferred for use in this invention are liquid polysiloxane-polyether copolymers having the following formula:

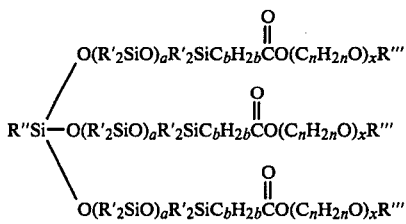

wherein R' and R'' are monovalent hydrocarbons, R''' is lower alkyl, preferably alkyl having 1 to 7 carbon atoms, a is at least 2, preferably 2 to about 40, b is from 2 to 3, n is from 2 to 4, and x is at least 5, preferably 5 to 100.

By way of illustration, R' and R'', independently, are alkyl, such as methyl, ethyl, propyl, butyl, octyl, and the like; cycloalkyl, such as cyclohexyl, cycloheptyl, and the like; aryl, such as phenyl, tolyl, naphthyl, xylyl, and the like; aralkyl, such as benzyl, phenylethyl, and the like; alkenyl or cycloalkenyl, such as vinyl, allyl, cyclohexenyl, and the like; and halogenated derivatives of any of the foregoing, such as chloromethyl, chlorophenyl, dibromophenyl, and the like. Illustratively, R''' is methyl, ethyl, propyl, butyl, isobutyl, amyl, and the like.

The preparation of the above polysiloxane-polyether copolymer is described in U.S. Pat. No. 3,629,165, incorporated herein by reference. Suitable commercially available materials are SF-1066 and SF-1141, from General Electric Company, Mallinckrodt's BYK-300, Union Carbide's L-540 and Dow-Corning's DC-190.

Other ingredients, such as thickening agents, pigments, dyes, and the like, can also be included for their conventionally employed purposes. These are added to the compositions after hydrolysis has been completed.

The coating compositions can be applied to the surface of an article after priming, e.g., with a thermosetting acrylic, using conventional methods, e.g., as by flow coating, spraying or dip coating, to form a continuous film or layer thereon. The cured compositions are useful as protective coatings on a wide variey of surfaces, either transparent or opaque, including plastic surfaces and metal surfaces. Examples of such plastics include synthetic organic polymeric substrates, such as acrylic polymers, e.g., poly(methylmethacrylate), and the like; polyesters, e.g., poly(ethylene terephthalate), poly(butylene terephthalate), and the like; polyamides, polyimides, acrylonitrile-sytrene copolymers; styrene-acrylonitrile-butadieneterpolymers; polyvinyl chloride; butyrates, polyethylene, and the like.

Special mention is made of the polycarbonates, such as those polycarbonates known as Lexan®, available from General Electric Company, including transparent panels made of such materials. The compositions of this invention are especially useful as protective coatings on the primed surfaces of such articles.

Suitable substrates also include both bright and dull metal surfaces, such as aluminum or sputtered chromium alloys. In addition, the coating compositions of this invention can be applied on other types of surfaces such as wood, leather, glass, ceramics, textiles, and the like.

A hard coating is obtained by removing the solvent and other volatile materials from the composition. The coating air-dries to a substantially tack-free condition, but heating in the range of 75° C. to 200° C. is necessary to obtain condensation of residual silanols in the partial condensate. Final cure results in the formation of silsesquioxane($RSiO_{3/2}$). In the cured coating, the ratio of $RSiO_{3/2}$ to $SiO_2$, where R is methyl, equal to 2, is most preferred. The coating thickness can be varied, but, in general, the coating will have a thickness in the range between 0.5 to 20 microns, more usually from 2 to 10 microns.

DESCRIPTION OF THE PREFERRED EMBODIMENTS

The compounds and primed articles coated with the compositions of this invention are illustrated in the following examples. All parts are by weight.

EXAMPLE 1

(a) 4-Allyloxy-2-hydroxybenzophenone(II).

A mixture of 21.4 g. (0.1 mole) of 2,4-dihydroxybenzophenone, 13.2 g. (0.11 mole) of freshly distilled allyl bromide, and 14 g. (0.1 mole) of potassium carbonate in 100 ml. of dry acetone is refluxed under nitrogen for 10 hours. After cooling, the inorganic salts are filtered off and the organic solution is washed with water and extracted with chloroform. After drying and evaporating the solvent, the light yellow oil is crystallized from ether to give light yellow crystals, 18 g. (73% yield), m.p. 68°–70° C. NMR δ, 12.47 (S.1H), 7.67 (m.6H), 6.60 (m.2H), 6.05 (m.1H), 5.50 (m.2H), 2.66 (D.2h). Carbon-Hydrogen analysis: C, 75.4, (calc. 75.58); H, 5.7 (calc. 5.6).

(b) 4-[γ(Triethoxysilyl)propoxy]-2-hydroxybenzophenone.

To a mixture of 5.08 g. (0.02 mole) of compound (II) and 3.28 g. (0.02 mole) of triethoxysilane in 100 ml. of dry toluene is added 10 drops of 5% platinum vinylsiloxane complex hydrosilation catalyst under nitrogen with stirring. The solution becomes warm, and the reaction is completed in one half hour. Evaporation of the solvent at 50° C. under a vacuum leaves a light yellow viscous oil containing traces of dark particles, presumably from the Pt catalyst, which are removed by filtration. The yield is 8.07 g. (96% of theoretical). NMR δ, 12.47 (S.1H), 7.67 (m.6H), 6.60 (m.2H), 3.93(m.8H), 2.00 (m.2H), 1.27 (t.9H), 0.86 (m.2H). Carbon-Hydrogen analysis: C, 62.8 (calc. 63.1); H, 7.0 (calc. 7.2). The product is suitable for use as a uv stabilizer according to this invention.

EXAMPLE 2

2,2',4,4'-Tetrahydroxybenzophenone, 24.6 g., (UVINOL D-50), 100 ml. of N,N-dimethylformamide and 21.6 g. of sodium methoxide (25% in methanol) are heated to 135° C. to distill off methyl alcohol, then the mixture is cooled to 80° C. Then 17.1 g. of chloromethyltrimethoxysilane is added over a 5 minute period. The temperature is increased from 90° C. to 125° C. and the mixture is refluxed for three hours, during which time a solid separates out. Stirring is stopped and the mixture is filtered under nitrogen. The filtrate is vacuum distilled to remove dimethylformamide. The pressure is reduced to 28 mm. and then to 8 mm Hg. and distillation is continued. There is obtained 44 g. of trimethoxysilylmethyl-functionalized 2,2',4,4'-tetrahydroxybenzophenone. It is suitable for use as a uv stabilizer according to this invention.

EXAMPLE 3

The general procedure of Example 2 is repeated, with 21.4 g. of 2,4-dihydroxybenzophenone, 100 ml. of N,N-dimethylformamide, 21.6 g. of sodium methoxide (25% in methanol) and 17.1 g. of chloromethyltrimethoxysilane. There is obtained a residue which is soluble in methyltrimethoxysilane. The reaction product comprises trimethoxysilylpropyl-functionalized 2,4-dihydroxybenzophenone. It is suitable for use as a uv stabilizer according to this invention.

EXAMPLE 4

4,4'-Dihydroxybenzohenone, 21.4 g., 0.1 mole, is dissolved in 98.9 g. of diethyleneglycol dimethyl ether. The system is swept with nitrogen and 21.6 g. of a 25% solution of sodium methoxide in methanol is added during five minutes. The reaction mixture is allowed to stand for sixteen hours, then 39.7 g. of methanol is distilled off. A portion of canary yellow solid separates as the methanol is distilled off. Distillation is continued to a pot temperature of 140° C., head temperature 72° C., maximum. The mixture is then cooled to 50° C. Chloromethyltrimethoxysilane, 17.1 g., is added all at once and rinsed in with methanol containing a small amount of diethyleneglycol dimethyl ether. The mixture is heated to 170° C., whereupon it boils gently. It is shut down after 1½ hours at 170° C. There is obtained a solution of trimethoxysilylmethyl-functionalized 4,4'-dihydroxybenzophenone. The product is suitable for use as uv stabilizer according to this invention.

EXAMPLE 5

Twenty-two and one-tenths parts by weight of Ludox 15 silica Sol (DuPont, an aqueous dispersion of colloidal silica having an average particle size of 12 millimicrons and a pH of 8.4), is added to a solution of 0.1 part by weight of methyltriacetoxysilane in 26.8 parts by weight of methyltrimethoxysilane. The temperature of the reaction mixture is kept at 20° to 25° C. The hydrolysis is allowed to continue for 24 hours. Five parts by weight of a polysiloxane-polyether copolymer (SF-1066) General Electric Company) is included as a flow control agent. The resulting reaction mixture has a solids content of 40.5 percent. Isobutanol is added to bring the solids content to 20 percent. The pH of the composition is about 7.2.

Two compositions are made by mixing 300 g. and 3.5 and 5.9 grams, respectively, of 4-[γ-(triethoxysilyl)-propoxy]-2-hydroxybenzophenone. Each composition is flow coated onto 6"×8" transparent LEXAN ® poly(bisphenol-A carbonate) panels which have been primed with a thermosetting acrylic emulsion (Rohm & Haas 4% Rhoplex). The panels are air dried for 30 minutes, and then cured at 120° C. for one hour. After 500 Taber Abraser cycles (500 g. load, CS-10F wheels), according to ANSI-Z226.1-1977 section 5.17, the change in percent haze (Δ%H) is found to be 6.1 and 7.1, respectively, for the 3.9 and 5.9 g. compositions. All samples pass the cross-hatched adhesion test (DIN-53-151) after 7 days immersion in water at 65° C. The 3.9 g. composition (6.5% based on solids) does not crack until after 744 hours, nor does it fail the cross-hatched adhesion test until after 987 hours of exposure under an array of six R-S sunlamps arranged at 120° from one another, when the coated panels are placed on a rotating platform (3 revolutions per minute) spaced 10 inches below the face of the lamps. The 5.9 g. composition (10% based on solid) does not show any cracks until after 790 hours of exposure, and no failure of adhesion until after 1340 hours. Both do not show adhesion failure until after a minimum of 118 hours exposure to ultraviolet light in a QUV accelerated Weathering Tester (4 hours. uv cycle at 50° C.; 4 hrs. condensation cycle at 45° C.).

All obvious variations of the invention are within the full intended scope of the appended claims.

We claim:

1. An ultraviolet light absorbing agent, comprising a compound having the formula:

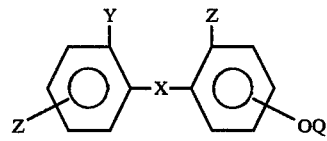

wherein

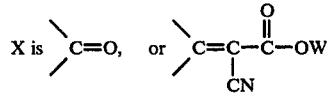

Y is OH;
Z is H, OH, OQ or OW;
Q is —$CH_2(CH_2)_nSi(R_2)_x(OR_1)_y$; and
W is —$C_mH_{2m+1}$;
where x=0, 1 or 2, y=1, 2 or 3, x+y=3, $R_1$=alkyl or alkanoyl having 1 to 6 carbon atoms, $R_2$=alkyl having 1 to 6 carbon atoms, n=0, 1 or 2 and m=1 to 18.

2. An ultraviolet light absorbing agent, comprising a compound having the formula:

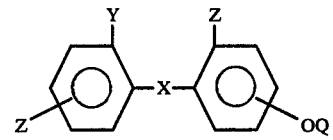

wherein:
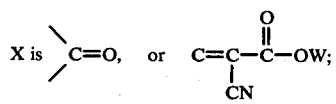
Y is H;
Z is H, OH, OQ or OW, where at least one Z is OH;
Q is $-CH_2(CH_2)_n Si(R_2)_x(OR_1)_y$; and
W is $-C_m H_{2m+1}$;
where $x=0$, 1 or 2, $y=1$, 2 or 3, $x+y=3$, $R_1$=alkyl or alkanoyl having 1 to 6 carbon atoms, $R_2$=alkyl having 1 to 6 carbon atoms, $n=0$, 1 or 2 and $m=1$ to 18.
3. A compound as defined in claim 2, wherein Z is OH.
* * * * *